June 19, 1956 H. C. SWIM Plant Pat. 1,485
PEACH TREE
Filed May 23, 1955
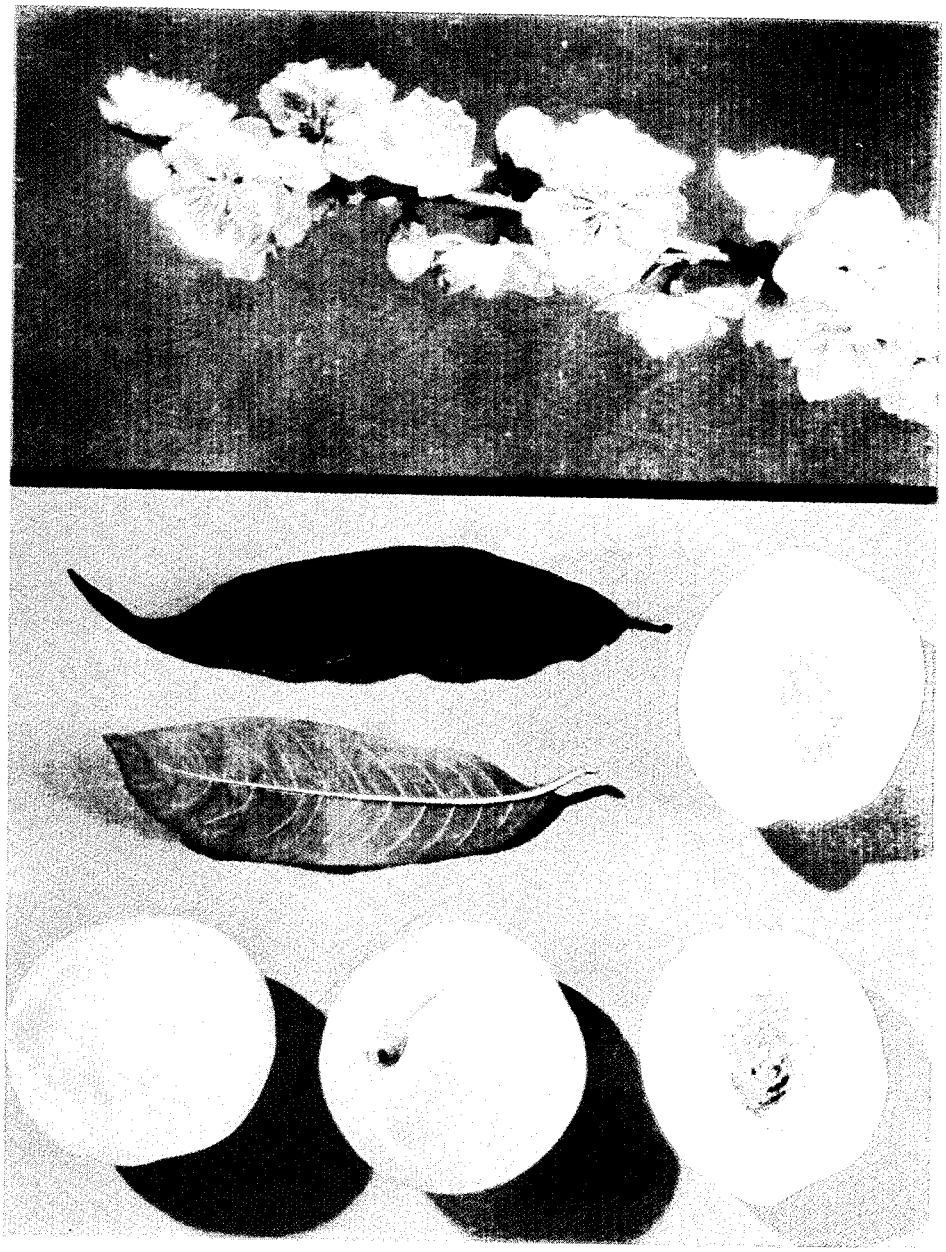
Inventor.
H. C. Swim
By: Robb & Robb
Attorneys United States Patent Office Plant Pat. 1,485
Patented June 19, 1956

1,485

PEACH TREE

Herbert C. Swim, Ontario, Calif., assignor to Armstrong Nurseries, Inc., Ontario, Calif., a corporation of California Application May 23, 1955, Serial No. 510,594

1 Claim. (Cl. 47—62)

The present invention relates to a new and distinct variety of peach tree of the yellow-fleshed, freestone fruit-bearing type which was originated by me by crossing two unnamed and unpatented varieties, each derived from an extended series of crosses beginning with an initial cross of "Early Imperial" (unpatented) by "Coolidge Double Red" (unpatented) in the case of one parent, and beginning with "Rio Oso Gem" (Plant Patent No. 84) by "Lukens Honey" (unpatented) in the case of the other parent.

The primary objective of this breeding was to produce an improved peach variety, and this objective was fully achieved with the resultant combination of the most desirable characteristics of the two parent varieties, along with other desirable features.

More specifically speaking, my new variety is particularly characterized as to novelty by its vigorous and upright growth, its relatively low winter-chilling requirements and attendant high and regular productivity in climates corresponding to that of Southern California, its large double blooms of medium pink color which are borne from 1 to 4 flowers per node, with the nodes relatively closely spaced and giving a distinct ornamental appearance to the tree during the blooming period, its large, round fruit of relatively firm texture and consequent good handling qualities, and the delectable flavor of its fruit.

In comparison with its seed parent, the fruit of my new variety ripens from early July to mid-July, whereas the fruit of this parent ripens from late July to early August, and the blooms of the new variety are large in size, double in petalage and a medium shade of pink color in contrast to the medium sized blooms, usually single petalage and light pink color of the blooms of this parent.

As compared with its pollen parent, the flesh of the fruit of my new variety is yellow and of relatively firm texture, whereas that of the parent variety is white and of relatively soft texture, and the fruit of the new variety has flesh which is free from the pit or stone instead of clinging to the stone like the flesh of the fruit of this parent.

In general, the ripening season of my new variety is from about one week to ten days later than that of the "Babcock" peach (unpatented), which is one of the most well-known varieties in Southern California, and the chilling requirements of the new variety are even somewhat less than that of the "Babcock" peach which is known to require little winter-chilling in Southern California.

The foregoing characteristics and distinctions definitely differentiate my new variety from its parents, as well as from all other varieties of which I am aware, and asexual reproduction of my new variety by grafting, as performed by me at Ontario, California, shows that these characteristics and distinctions come true to form and are established and transmitted through succeeding propagations.

The accompanying drawing shows typical specimens of the flowers, foliage and fruit of my new variety, with both the upper and lower surfaces of the foliage being illustrated and with both exterior and sectional views of the fruit being shown, all as depicted in color as nearly true as it is reasonably possible to make the same in a color illustration of this character.

The following is a detailed description of my new variety, as based upon observations of specimens grown at Ontario, California, with color terminology in accordance with Robert F. Wilson's Horticultural Colour Chart, except where color terminology is given from Ridgway's Color Standards and Nomenclature (hereafter abbreviated as "Ridgway") or where general color terms of ordinary dictionary significance are obvious:

Dates first and last picking: Vary somewhat from year-to-year because of varying winter-chilling in Southern California, but usually begin picking about July 7 to July 24, ending about July 17 to August 4, depending on the season.

Tree: Large; vigorous; upright; dense; vase-formed; productive; regular bearer.

*Trunk.*—Stocky; from medium to shaggy in surface roughness.

*Branches.*—Stocky; from medium to shaggy; dull. Color—near Light Grayish Olive, Plate XLVI (Ridgway). Lenticels—numerous; medium size.

*Leaves.*—Acuminate; lanceolate; medium thickness; relatively smooth; wavy type as described in article entitled "Progress Report on Identification of Peach Varieties by Leaf Characteristics," by Meader & Blake, published in American Society for Horticulture Proceedings for 1939, vol. 37, pages 203 to 207. Size—large. Length—from 5½ inches to 7 inches; width—from 1¼ inches to 1¾ inches. Color: upper surface—between Forest Green, Plate XVII (Ridgway) and Dark Dull Yellow-Green, Plate XXXII (Ridgway); under surface—between Light Elm Green, Plate XVII (Ridgway) and Chromium Green, Plate XXXII (Ridgway). Margin—finely serrate. Petiole—medium length; from ¼ inch to ½ inch long; from medium to thick caliper. Glands—average 3 in number; alternate; reniform; medium size; usually positioned on petiole at attachment of leaf blade and rarely on leaf blade near petiole. Color—green.

*Stipules.*—Short; narrow; early deciduous.

Flower buds: Large; long; conic; plump; free portion of calyx has grayish pubescence. Color—between Crimson, Plate 22/1, page 22 and Spiraea Red, Plate 025/1, page 112 at first, becoming near Phlox Pink, Plate 625/2, page 77 just before opening.

Flowers:

*Dates first and full bloom.*—About February 3 to February 26 and about February 14 to March 18; from medium to late as compared with other varieties.

*Size (when fully open).*—From 1¾ inches to 2 inches in diameter; large.

*Petalage.*—Double; usually from 14 to 16 petals, with 1 or 2 petaloids; from 1 to 4 flowers borne at each node, with nodes usually spaced from ½ inch to 1 inch apart on flowering branches, thus forming an almost continuous spray of flowers along each branch and giving the tree a definite ornamental appearance during blooming period.

*Petals.*—Arranged regularly. Shape—nearly oval; rounded at apex and at base; tapering toward attachment point; with margins of petals entire except for occasional notching at apical end; cupped and sometimes wavy, with petaloids twisted and irregular.

*Color.*—Newly opened flower—between Phlox Pink, Plate 625/2, page 77 and Rhodamine Pink, Plate 527/2, page 138. Mature flower—between Phlox Pink, Plate 625/3, page 77 and Rhodamine Pink, Plate 527/2, page 138, marked particularly near base with near Spiraea Red, Plate 025/1, page 112.

Fruit:

*Maturity when described.*—Eating ripe. Date—July 19.

*Size.*—Slightly variable; from medium to large. Axial diameter—from 2½ inches to 2¾ inches. Transverse diameter in suture plane—from 2⅜ inches to 2⅝ inches. Diameter at right angles to suture plane—from 2½ inches to 2¾ inches.

*Form.*—Uniform; symmetrical; globose.

*Suture.*—Usually an inconspicuous line; shallow; extends from base to apex, but is discontinuous at apex; has slight depression beyond pistil point.

*Ventral surface.*—Rounded; sometimes slightly lipped towards base.

*Cavity.*—Rounded. Depth—from ¼ inch to ⅜ inch. Breadth—from ⅜ inch to ½ inch. Markings—None.

*Base.*—Rounded.

*Apex.*—Short; rounded; with short apical pistil point.

*Stem.*—From 5/16 inch to 7/16 inch in length; from medium to stout; glabrous; strong adherence to stone.

*Skin.*—Thick; free. Texture—from medium to tough. Tendency to crack—slight in humid weather. Color—between Empire Yellow, Plate 603/1, page 66 and Straw Yellow, Plate 604/1, page 67, overlaid somewhat on surface exposed to the sun with between Vermillion, Plate 18/2, page 18 and Scarlet, Plate 19/2, page 19. Down—from scant to moderate; short; does not roll up when rubbed.

*Flesh.*—Color—between Lemon Yellow, Plate 4/3, page 4 and Indian Yellow, Plate 6/3, page 6, with flecks and stripes of near Carmine, Plate 21, page 21. Surface of pit cavity—Color—near Buttercup Yellow, Plate 5/3, page 5, marked with near Geranium Lake, Plate 20/2, page 20. Amygdalin—from moderate to scant. Juice—Abundant; rich. Texture—medium firmness; fine; melting. Fibres—few; fine; tender. Ripens—Evenly. Flavor — acid. Aroma — pronounced. Eating quality—good.

Stone: Free; adheres to flesh along both dorsal and ventral edges; short fibres; free on sides; retains short fibre-like threads in depressions of stone.

*Size.*—From medium to large. Length—from 1⅜ inches to 1⅝ inches. Breadth—from ⅞ inch to 1 inch. Thickness—from ¾ inch to ⅞ inch.

*Form.*—Ovoid; cuneate toward apex.

*Base.*—Nearly straight.

*Hilum.*—Narrow; oblong.

*Apex.*—Acute.

*Sides.*—Slightly unequal; curved on right and left sides.

*Surface.*—Irregularly furrowed toward apex; ridged toward apex; pitted from base to above center; sometimes with furrows and ridges near base.

*Ridges.*—Rounded toward apex.

*Pits.*—Elongated.

*Ventral edge.*—Thick; with wing generally throughout.

*Dorsal edge.*—Medium; with narrow groove to above center; ridges on either side interrupted.

*Tendency to split.*—None.

*Color.*—Near Verona Brown, Plate XXIX (Ridgway).

Use: Local; dessert.

Keeping quality: Medium.

Insect resistance: Medium resistance to thrips, as determined by comparison with other varieties grown under comparable cultural conditions at Ontario, California.

Disease resistance: From medium to poor resistance to brown rot, as determined by comparison with other varieties grown under comparable cultural conditions at Ontario, California.

Shipping quality: Medium.

I claim:

A new and distinct variety of peach tree of the yellow-fleshed, freestone fruit-bearing type, substantially as herein shown and described, characterized particularly as to novelty by its vigorous and upright growth, its relatively low winter-chilling requirements and attendant high and regular productivity in climates corresponding to that of Southern California, its large, double blooms of medium pink color which are borne from 1 to 4 flowers per node, with the nodes relatively closely spaced and giving a distinct ornamental appearance to the tree during the blooming period, its large, round fruit of relatively firm texture and consequent good handling qualities, and the delectable flavor of its fruit.

No references cited.